(12) United States Patent
Grippo et al.

(10) Patent No.: US 6,363,802 B1
(45) Date of Patent: Apr. 2, 2002

(54) APPARATUS FOR ASPIRATING LIQUID FROM A VESSEL

(75) Inventors: Paul M. Grippo, Lake Elmo, MN (US); Richard A. Marquis; Marco Zuleta, both of Miami, FL (US); Christopher J. Falvai, Plantation, FL (US)

(73) Assignee: Coulter International Corp., Miami, FL (US)

( * ) Notice: Subject to any disclaimer, the term of this patent is extended or adjusted under 35 U.S.C. 154(b) by 0 days.

(21) Appl. No.: 09/275,707

(22) Filed: Mar. 25, 1999

(51) Int. Cl.[7] .................................................. G01N 1/00
(52) U.S. Cl. .................................................. 73/864.24
(58) Field of Search ............ 73/863.01, 864.23–864.25

(56) References Cited

U.S. PATENT DOCUMENTS 4,326,851 A  4/1982  Bello et al. ................... 23/230
4,715,413 A  12/1987  Backlund et al.
5,133,392 A  * 7/1992  Hamann ................... 73/864.25

FOREIGN PATENT DOCUMENTS

EP  0 843 176 A1  5/1998

* cited by examiner

*Primary Examiner*—Robert Raevis
(74) *Attorney, Agent, or Firm*—Warren W. Kurz; Mitchell E. Alter

(57) ABSTRACT

Apparatus for precisely aspirating small volumes of liquid, e.g., a blood sample, contained in a vessel, e.g., a test tube or vial, includes a mechanism for sensing that the tip of an aspirating probe is contacting the bottom of the vessel during the aspiration process. Such a bottom-sensing mechanism is adapted to sense a predetermined forcible interaction between the probe tip and the vessel bottom. In a preferred embodiment, such forcible interaction is sensed by detecting movement of a movably mounted platform that supports the vessel during aspiration. In a second embodiment, the forcible interaction is sensed by detecting the back-emf in a motor winding used to advance the aspiration probe.

9 Claims, 5 Drawing Sheets

APPARATUS FOR ASPIRATING LIQUID FROM A VESSEL

BACKGROUND OF THE INVENTION

1. Field of the Invention

The present invention relates to improvements in apparatus for reliably aspirating small aliquots (in the microliter range) of liquid sample from a vessel, e.g. a test tube or vial. The liquid aspirating apparatus of the invention is particularly useful in biological and chemical instruments that are required to automatically withdraw small, yet precise, volumes of liquid from a test tube or vial for subsequent use or analysis.

2. Discussion of the Prior Art

Liquid transport systems are known for aspirating small volumes of a liquid sample from a vessel at one location and for dispensing the aspirated sample into a reaction chamber at another location. Such systems are used, for example, in hematology instruments adapted to automatically analyze a blood sample. In such instruments, the tip of an aspiration probe or needle is lowered into a vial containing a blood sample to a level below that of the sample in the vial. A negative pressure (vacuum) is then applied to the probe to draw all or a portion of the sample into and through the probe to a location where the aspirated sample can be segmented into smaller and precise volumes for analysis.

To aspirate relatively minute volumes of liquid samples contained in a vial, or to assure that the entire contents of a liquid-containing vial are extracted by an aspirating system of the type described above, it is necessary that the tip of the aspirating probe contacts the inside bottom of the vial during the aspiration process. In those systems in which the vials and aspirating probes are of standard size, virtual contact between the probe tip and the vial bottom can be assured by precisely controlling both the position of the vial and the vertical displacement of the aspirating probe. However, in those systems in which the vial size (length) is variable, achieving the desired contact can be problematic. Various schemes have been devised for detecting that the tip of the aspirating probe is always immersed in the liquid during aspiration; see, for example, the disclosure of the commonly assigned U.S. Pat. No. 4,326,851 to Bello et al. In all these schemes it is common to arrest downward movement of the aspirating probe before the probe tip contacts the bottom of the vial for fear of breaking the vial; as a result, small volumes of sample in the vial cannot be removed, and/or the last drop of a relatively large volume of liquid cannot be aspirated.

SUMMARY OF THE INVENTION

In view of the foregoing discussion, an object of this invention is to provide an improved liquid aspiration apparatus of the type described, one that is improved from the standpoint that the last drop of liquid in a vessel can be reliably aspirated.

According to the invention, a conventional liquid aspiration apparatus is modified to include a mechanism for determining that the tip of a liquid-aspiration probe is continuously maintained in engagement with the inside bottom of a liquid-containing vessel during aspiration of the liquid therein. Such a bottom-sensing mechanism is adapted to sense a predetermined forcible interaction between the probe tip and the vessel bottom. In a preferred embodiment, such forcible interaction is sensed by detecting movement of a movably mounted platform that supports the vessel during aspiration. In a second embodiment, the forcible interaction is sensed by detecting the back-emf in a motor winding used to advance the aspiration probe.

In accordance with the preferred embodiment of the invention, the improved liquid aspirating apparatus of the invention comprises:

(a) a platform for supporting a liquid-containing vessel in an upright orientation so that a longitudinal axis of the vessel is substantially vertical, such platform being movably mounted on a frame for vertical movement relative to a nominal position;

(b) spring means for biasing the platform towards its nominal position;

(c) aspirating means including an aspirating probe movable along the longitudinal axis of the vessel supported by the movably-mounted platform, such probe having a tip through which liquid can be aspirated from the vessel;

(d) drive means for selectively advancing the aspirating probe along the vessel's longitudinal axis to cause the probe tip to engage the inside bottom of the vessel and to exert a downward force on the vessel, thereby causing the platform to move away from its nominal position against the force exerted by the spring means;

(e) movement-detecting means for detecting a predetermined movement of the platform relative to its nominal position to sense that the probe tip has been sufficiently advanced to forcibly engage the inside bottom of the vessel, such movement detecting means producing a signal responsive to such movement detection; and (f) circuit means responsive to the signal for controlling the drive means to maintain such forcible engagement during liquid aspiration.

According to the alternative embodiment, the above-noted drive means comprises an electric motor having a motor winding, and movement-detecting means is replaced with a circuit for detecting the back electromotive force in the motor winding as caused by the resistance of the vessel bottom to further movement of the aspirating probe after initial contact is made between the probe tip and the vessel bottom.

The invention and its various advantages will become apparent to those skilled in the art from the ensuing description of a preferred embodiment, reference being made to the accompanying drawings.

DETAILED DESCRIPTION OF PREFERRED EMBODIMENTS

Figure 1:
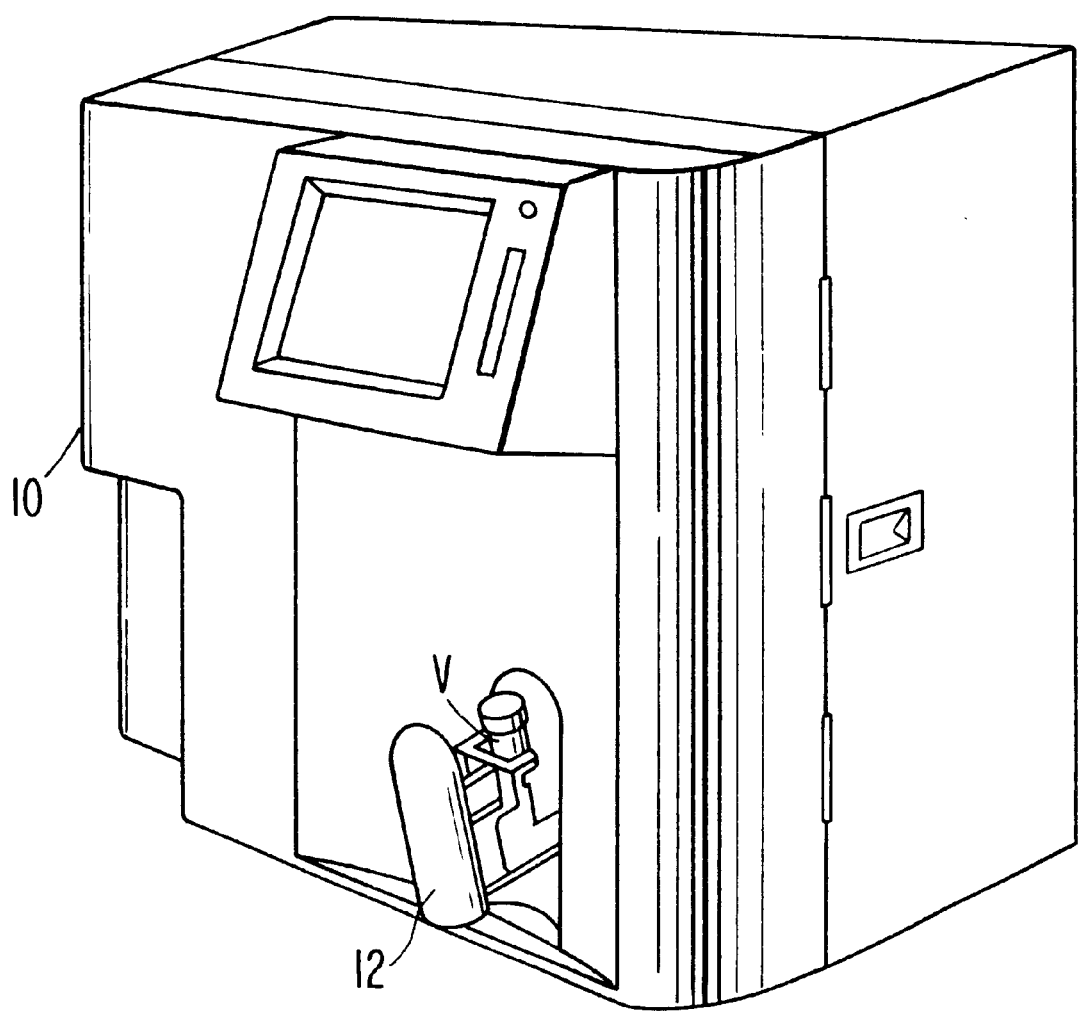
FIG. 1 is a perspective illustration of an instrument in which the invention is useful.
Figure 3A:
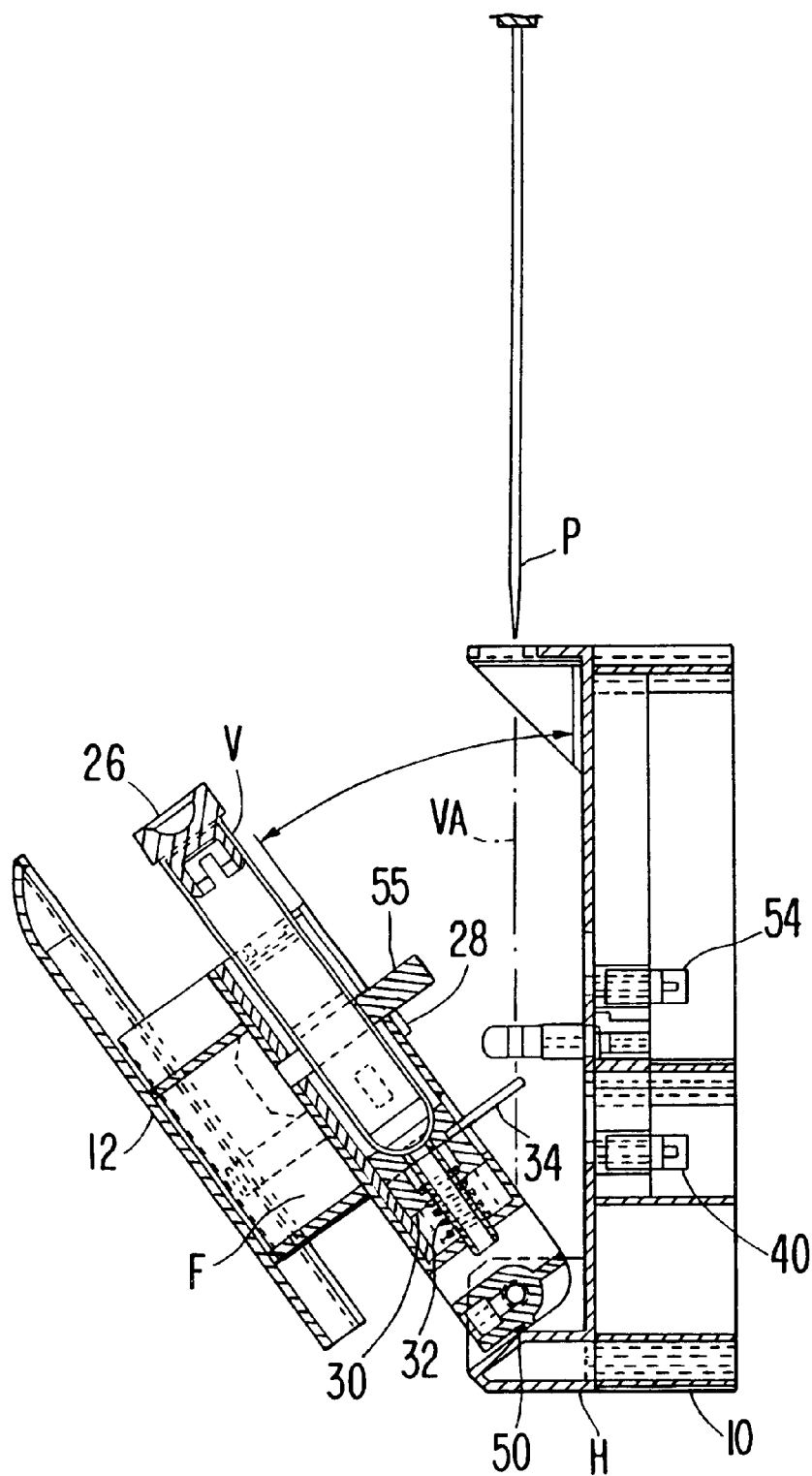
FIGS. 3A, 3B and 3C are cross sectional illustrations of the FIG. 2 apparatus showing a liquid-containing vessel and an aspiration probe in different relative positions.
Figure 3C:
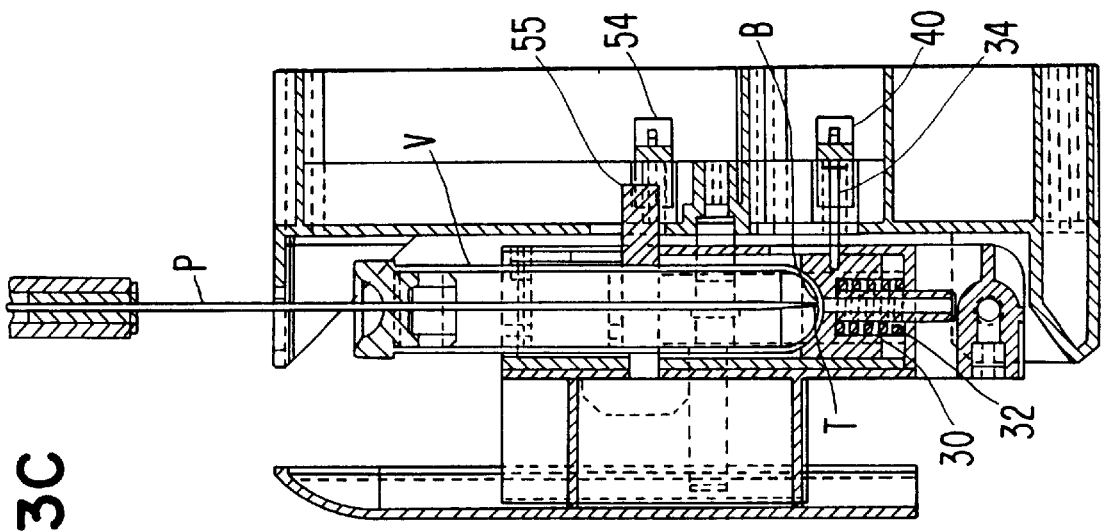
Figure 3B:
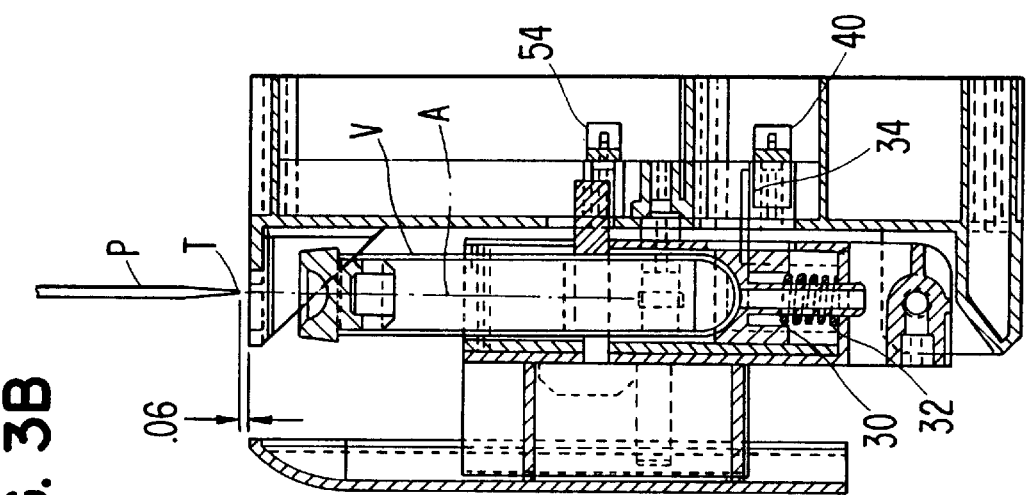

Referring now to the drawings, FIG. 1 illustrates a hematology instrument 10 adapted to analyze, in a conventional manner, a blood sample contained in a vessel, e.g. a test tube or vial. Such instrument comprises a sample loading/ unloading door 12 which is pivotally mounted on the instrument housing for movement between an open position, as shown in FIGS. 1, and 3A, and a closed position, as shown in FIGS. 3B and 3C. In its open position, the door is ready to receive or unload a vessel V containing a blood sample for analysis. In its closed position, the door locates the vessel vertically directly below to an aspiration probe of the instrument, in a path of vertical movement of the probe, as explained below.

Figure 2:
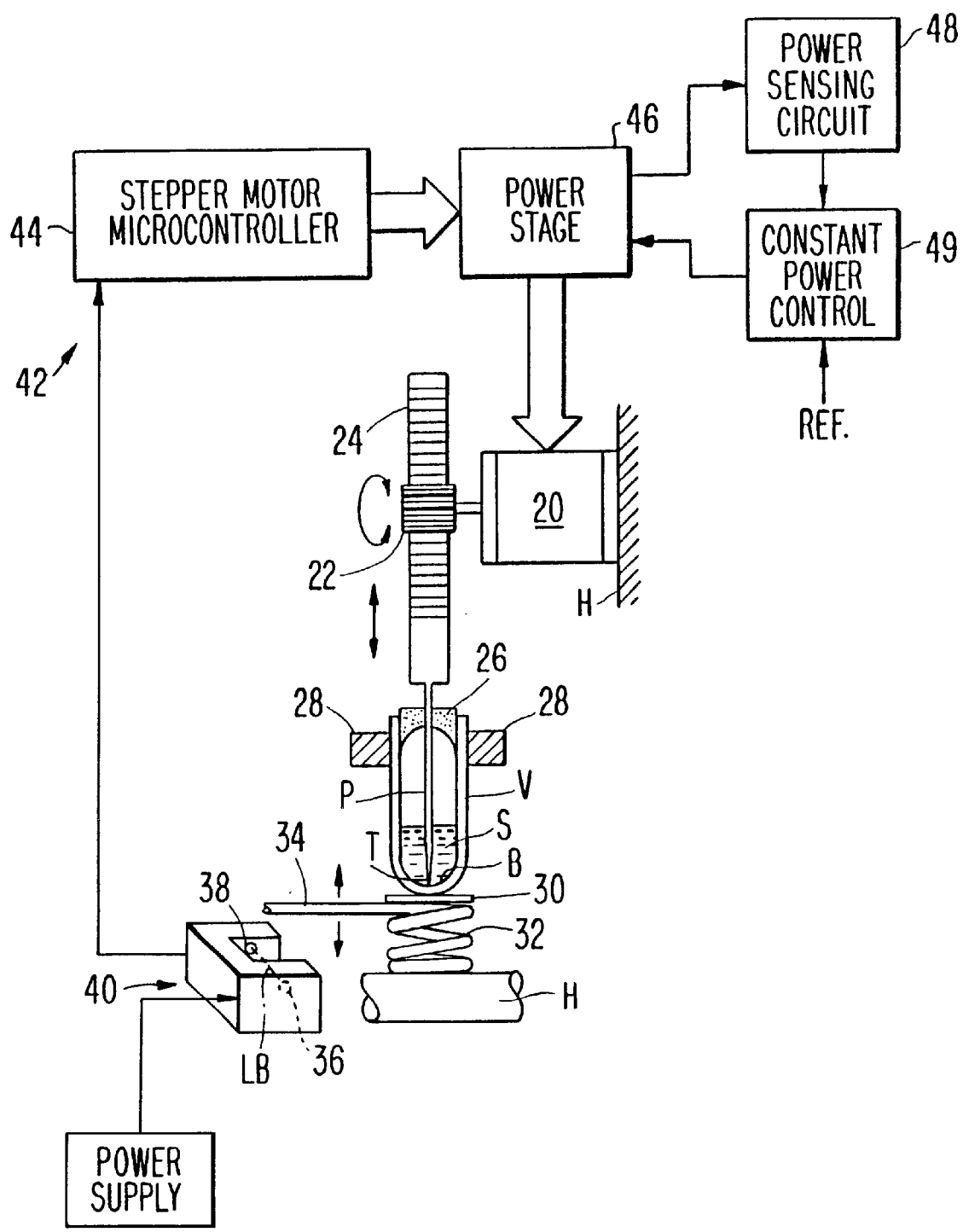
FIG. 2 is a schematic illustration of a preferred embodiment of the invention.

FIG. 2 schematically illustrates a preferred apparatus for assuring that the tip T of an aspiration probe P used to aspirate a liquid sample S contained in a vessel V remains in contact with the inside bottom B of the liquid sample-containing vessel during aspiration of the sample therein. As illustrated, a stepper motor 20 or the like operates to selectively rotate a toothed pinion 22 positioned to engage a slidably mounted gear rack 24 to which the aspiration probe is mechanically coupled. Thus, as pinion 22 rotates clockwise or counterclockwise, rack 24 moves up or down, thereby producing a vertical motion of the aspiration probe within the vessel. As the probe moves vertically downward from a position above the vessel, its tip T pierces a rubber stopper 26 enclosing one end of the sample-containing vessel. Continued downward movement of the aspiration probe causes the probe tip to engage the inside bottom of the vessel, thereby enabling very small volumes of sample to be aspirated. In accordance with the present invention, bottom-sensing means are provided for assuring that the probe tip T not only contacts the vessel bottom during aspiration, but also remains in contact with the vessel bottom during aspiration. In addition to assuring that the last drop of sample can be aspirated, such contact assures that air is not intermittently drawn into the aspiration probe, whereby any chance of a short or partial aspiration is minimized.

Still referring to FIG. 2, vessel V is laterally supported between a pair of spring clips 28 which provides lateral support to the vessel while enabling it to move axially along its longitudinal axis. The base of vessel V is supported on a platform 30 that rests upon a coil or compression spring 32 supported by the instrument housing H. Spring 32 serves to support the vessel in a nominal vertical position when no external downward force is applied to the vessel, i.e. when the aspiration probe is not in contact with either the vessel stopper 26, or with the vessel bottom. Thus, the spring constant of the spring 32 is chosen so that the upward force it exerts on the bottom of platform 30 is offset by the downward force of the vessel and its contents in order to position the platform in its nominal position (as shown in FIG. 2). Spring 32 carries a horizontally-extending flag member 34 which operates, during downward movement of the platform 30, to interrupt a light beam LB produced between an optical source 36 and a receiver 38 of a conventional optical sensor 40. The output of the optical sensor is used to control a motor control circuit 42 that functions to selectively energize and de-energize stepping motor 20. As will be appreciated, when the aspiration probe is moved from a position above the vessel to a position in which the probe tip T initially contacts and then pierces the top surface of vessel stopper 26, a downward force will be exerted on the vessel and its underlying compression spring, thereby causing the spring to compress, and flag member 34 to move vertically downward. In order to prevent premature stoppage of the downward movement of the aspirating probe during piercing of the vessel stopper, the position of the optical sensor must be below that level reached by the flag member during the piercing to stopper. After piercing the stopper, a lesser downward force will be exerted on the vessel until the probe tip eventually contacts the vessel bottom. Thereafter, as the probe is continued to be driven downward against the vessel bottom, the vessel will begin to move downward, against the upward force exerted by the spring, until the flag member reaches a position in which it interrupts the optical beam of the optical sensor 40. At this time, the optical sensor will produce a signal causing the motor control circuit to arrest further downward movement of the probe. Thus, the spring constant of spring 32 must be chosen so that (a) it is not so compliant as to allow the flag member to reach the optical sensor during piercing of the stopper, whereby downward movement of the probe would be prematurely interrupted, and (b) it is not so stiff that the probe tip will break or otherwise damage the vessel before the flag member reaches its optical beam-interrupting position.

Motor control circuit 42 preferably comprises a conventional micro-controller 44 programmed to respond to input signals representing a desired displacement, direction, acceleration and velocity profiles for the aspiration probe. Upon command, the micro-controller generates digital signals to a power stage 46 which, in turn, delivers a corresponding signal to energize the windings of the stepper motor 20. The power stage comprises a level translator that accepts digital signal and converts them to suitable levels to drive a set of power transistors used to energize the stepper motor windings. A power sensing circuit 48 measures the current flowing through the motor windings by means of a series resistor that develops a voltage proportional to the current across its terminals. A constant power control stage 49 operates to compare this voltage with a reference voltage and modulates the power stage to maintain the power at a constant value. The micro-controller responds to the opto-sensor output to produce a holding current in the motor windings to maintain contact between the probe tip and the vessel bottom during sample aspiration.

Referring to FIGS. 3A–3C, a preferred apparatus is shown for mechanically implementing the concept schematically illustrated in FIG. 2. As shown, the vessel supporting components 28, 30 and 32 are mounted on a frame F rigidly connected to the aforementioned instrument door 12. Frame F is pivotally mounted on the instrument housing H for limited pivotal movement about pivot pin 50 for movement from the open position, shown in FIG. 3A, and the closed position shown in FIGS. 3B and 3C. A second opto-sensor 54 cooperates with a flag member 55 carried by the door frame to assure that the door is fully closed before aspiration of the sample can begin. When the door is in a closed position, the vessel's longitudinal axis A coincides with the vertical axis VA traversed by the aspiration probe. In FIG. 3B, the aspiration probe is shown in a position prior to entry into vessel V, and in FIG. 3B, the aspirating probe is shown in a position contacting the vessel bottom and as having forced the vessel downward, against the force of spring 32, to a point at which the flag member 34 has obstructed the light beam provided by the opto-sensor 40.

Figure 4:
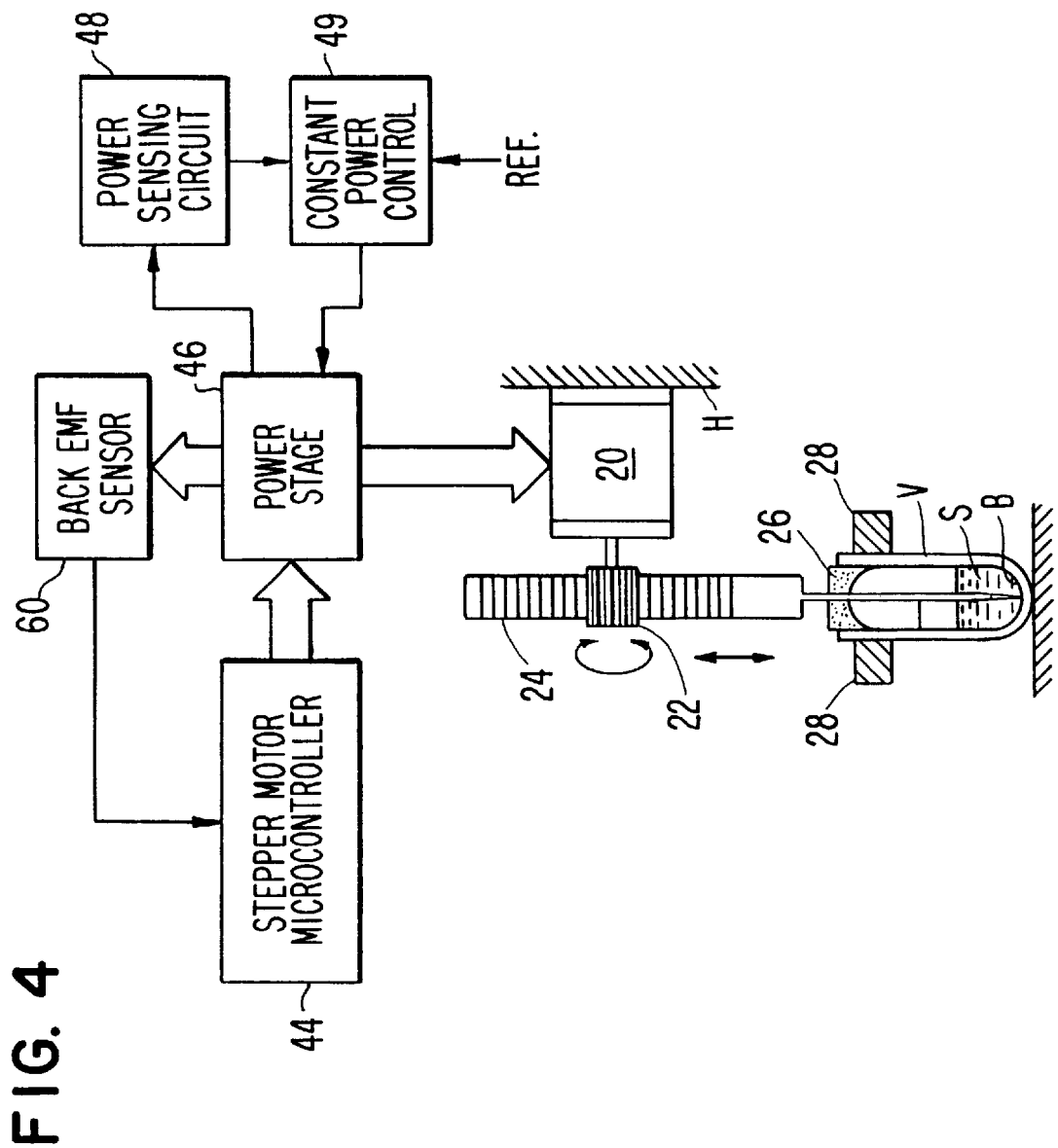
FIG. 4 is a schematic illustration of an electrical approach for sensing contact between the tip of an aspirating probe and the inside bottom of a liquid-containing vessel.

An alternative approach for sensing that the probe tip T has engaged the bottom of the vessel is to monitor the back-electromotive force (emf) in a coil or winding of a motor used to control the vertical movement of the aspirating probe. Such an approach is illustrated in FIG. 4 in which a back-emf sensor 60 is shown. Upon sensing that the back-emf has reached a threshold level, the output of the sensing circuit is used to maintain the motor current at a preset level, whereby contact between the probe tip and the vessel bottom is assured. In such an approach, the spring-biased support platform 30 and optical sensor 40 is obviated.

The invention has been described with reference to preferred embodiments. It is apparent that modifications and variations can be made without departing from the spirit of the invention.

What is claimed is:

1. Apparatus for aspirating liquid from a liquid-containing vessel, said apparatus comprising:
   (a) aspirating means including a probe having a tip through which liquid in a vessel can be aspirated from said vessel;
   (b) drive means for selectively advancing said aspirating probe along a longitudinal axis of the vessel to cause said probe tip to engage the inside bottom of said vessel and to exert a downward physical force on said vessel; and
   (c) sensing means for sensing said downward physical force and for producing a signal in response thereto;
   said drive means being responsive to said signal to maintain said downward physical force during liquid aspiration.

2. Apparatus for aspirating liquid from a liquid-containing vessel, said apparatus comprising:
   (a) aspirating means including a probe having a tip through which liquid in a vessel can be aspirated from said vessel;
   (b) drive means for selectively advancing said aspirating probe along a longitudinal axis of the vessel to cause said probe tip to engage the inside bottom of said vessel and to exert a downward force on said vessel; and
   (c) sensing means for sensing a predetermined force between said probe tip and said vessel bottom to assure contact between said probe tip and said vessel bottom during aspiration of liquid from said vessel by said aspirating means, said sensing means comprising means for sensing movement of said vessel as a result of contact between said probe tip and said vessel bottom.

3. Apparatus for aspirating liquid from a liquid-containing vessel, said apparatus comprising:
   (a) aspirating means including a probe having a tip through which liquid in a vessel can be aspirated from said vessel;
   (b) drive means for selectively advancing said aspirating probe along a longitudinal axis of the vessel to cause said probe tip to engage the inside bottom of said vessel and to exert a downward force on said vessel, said drive means comprising an electric motor; and
   (c) sensing means for sensing a predetermined force between said probe tip and said vessel bottom to assure contact between said probe tip and said vessel bottom during aspiration of liquid from said vessel by said aspirating means, said sensing means comprising means for sensing the back-electromotive force produced in said electric motor as a result of forcible contact between said probe tip and said vessel bottom.

4. Apparatus for aspirating liquid from a liquid-containing vial, said apparatus comprising:
   (a) a platform for supporting a liquid-containing vessel in an upright orientation so that a longitudinal axis of the vessel is substantially vertical, said platform being movably mounted on a frame for vertical movement relative to a nominal position;
   (b) spring means for biasing the platform towards its nominal position;
   (c) aspirating means including an aspirating probe movable along the longitudinal axis of the vessel supported by the movably-mounted platform, said probe having a tip through which liquid can be aspirated from the vessel;
   (d) drive means for selectively advancing the aspirating probe along the vessel's longitudinal axis to cause the probe tip to engage the inside bottom of the vessel and to exert a downward force on the vessel, thereby causing the platform to move away from its nominal position against the force exerted by said spring means;
   (e) movement-detecting means for detecting a predetermined movement of the platform relative to its nominal position to sense that the probe tip has been sufficiently advanced to forcibly engage the inside bottom of the vessel, said movement detecting means producing a signal responsive to said predetermined movement; and
   (f) circuit means responsive to said signal for controlling the drive means to maintain said forcible engagement during liquid aspiration.

5. The apparatus as defined by claim 4 wherein said drive means comprises an electrical motor that responds to an applied electrical current to advance said aspirating probe.

6. The apparatus as defined by claim 4 wherein said detecting means produces an electrical signal in response to detecting said predetermined movement, and wherein said electrical signal is used to disrupt the application of said electrical current to said electrical motor to arrest further movement of said probe.

7. The apparatus as defined by claim 4 wherein said detecting means comprises a photoelectric sensor.

8. The apparatus as defined by claim 4 wherein said platform is supported by a frame that is pivotally mounted about a pivot axis disposed normal to said longitudinal axis, whereby said platform can be tilted relative to a horizontal plane to facilitate loading of a vial thereon.

9. The apparatus as defined by claim 4 wherein said spring means comprises a compression spring.

* * * * *